(12) United States Patent
Mukkamala et al.

(10) Patent No.: US 11,779,230 B2
(45) Date of Patent: Oct. 10, 2023

(54) CENTRAL BLOOD PRESSURE MONITORING VIA A STANDARD AUTOMATIC ARM CUFF

(71) Applicants: Board of Trustees of Michigan State University, East Lansing, MI (US); University of Maryland, College Park, MD (US)

(72) Inventors: Ramakrishna Mukkamala, Okemos, MI (US); Keerthana Natarajan, East Lansing, MI (US); Jin-Oh Hahn, Rockville, MD (US)

(73) Assignee: Board of Trustees of Michigan State University, East Lansing, MI (US)

( * ) Notice: Subject to any disclaimer, the term of this patent is extended or adjusted under 35 U.S.C. 154(b) by 523 days.

(21) Appl. No.: 16/629,403

(22) PCT Filed: Jul. 12, 2018

(86) PCT No.: PCT/US2018/041793
§ 371 (c)(1),
(2) Date: Jan. 8, 2020

(87) PCT Pub. No.: WO2019/014432
PCT Pub. Date: Jan. 17, 2019

(65) Prior Publication Data
US 2020/0138305 A1    May 7, 2020

Related U.S. Application Data

(60) Provisional application No. 62/531,413, filed on Jul. 12, 2017.

(51) Int. Cl.
*A61B 5/022*    (2006.01)
*A61B 5/00*    (2006.01)

(52) U.S. Cl.
CPC ........ *A61B 5/02225* (2013.01); *A61B 5/7235* (2013.01)

(58) Field of Classification Search
CPC ....... A61B 5/02225; A61B 5/02; A61B 5/022; A61B 5/02208; A61B 5/6824;
(Continued)

(56) References Cited

U.S. PATENT DOCUMENTS

2003/0023173 A1 * 1/2003 Bratteli .................. A61B 7/045
600/485
2009/0149763 A1 * 6/2009 Chen ...................... A61B 5/022
600/494
(Continued)

FOREIGN PATENT DOCUMENTS

WO    WO-2017044823 A1 *    3/2017   ............... A61B 5/02

OTHER PUBLICATIONS

Shih et al. "Is Noninvasive Brachial Systolic Blood Pressure an Accurate Estimate of Central Aortic Systolic Blood Pressure?", Nov. 2016, American Journal of Hypertension, 29, 11, pp. 1283-1291 (Year: 2016).*
Millasseau. "Arterial pulse wave analysis", 2003, King's College of London (Thesis) (Year: 2003).*
Gao et al. "A Simple Adaptive Transfer Function for Deriving the Central Blood Pressure Waveform from a Radial Blood Pressure Waveform",Sep. 14, 2016, Scientific Reports, 6: 33230 (Year: 2016).*
(Continued)

*Primary Examiner* — Patrick Fernandes
(74) *Attorney, Agent, or Firm* — Harness, Dickey & Pierce PLC

(57) ABSTRACT

Current oscillometric devices for monitoring central blood pressure (BP) maintain the cuff pressure at a constant level to acquire a pulse volume plethysmography (PVP) waveform and calibrate it to brachial BP levels estimated with population average methods. A physiologic method was developed to further advance central BP measurement. A patient-specific method was applied to estimate brachial BP levels from a cuff pressure waveform obtained during conventional deflation via a nonlinear arterial compliance
(Continued)

model. A physiologically-inspired method was then employed to extract the PVP waveform from the same waveform via ensemble averaging and calibrate it to the brachial BP levels. A method based on a wave reflection model was thereafter employed to define a variable transfer function, which was applied to the calibrated waveform to derive central BP.

20 Claims, 11 Drawing Sheets

(58) Field of Classification Search
CPC . A61B 5/021; A61B 5/02108; A61B 5/02116; A61B 5/7235; A61B 5/7271; A61B 5/0225; A61B 5/02216; A61B 5/02158; A61B 5/02156; A61B 5/02141; A61B 5/02133; A61B 5/02125
See application file for complete search history.

(56) References Cited

U.S. PATENT DOCUMENTS

| | | | |
|---|---|---|---|
| 2010/0106030 A1 | 4/2010 | Mason | |
| 2011/0275944 A1* | 11/2011 | Qasem | A61B 5/0225 600/493 |
| 2018/0263513 A1* | 9/2018 | Qasem | A61B 5/02108 |

OTHER PUBLICATIONS

Gao et al. "Estimation of Pulse Transit Time as a Function of Blood Pressure Using a Nonlinear Arterial Tube-Load Model." IEEE transactions on bio-medical engineering, Jul. 2017, 64,7, pp. 1524-1534 (Year: 2017).*

Cheng et al. "Measurement Accuracy or a Stand-Alone Oscillometric Central Blood Pressure Monitor: a Validation Report for Microlite WatchBP Office Central", Jan. 2013, American Journal or Hyperension, 26, 1, pp. 42-50 (Year: 2013).*

* cited by examiner

Patient-Specific  Physiologic  Physiologic With GTF Instead Of VTF

Low PP Amplification (1.1 ± 0.03)

Middle PP Amplification (1.2 ± 0.05)

High PP Amplification (1.4 ± 0.11)

CENTRAL BLOOD PRESSURE MONITORING VIA A STANDARD AUTOMATIC ARM CUFF

CROSS REFERENCE TO RELATED APPLICATIONS

This application is a 371 National Phase of PCT/US2018/041793, filed on Jul. 12, 2018, and published in English as WO 2019/014432 A1 on Jan. 17, 2019, which claims the benefit of U.S. Provisional Application No. 62/531,413, filed on Jul. 12, 2017. The entire disclosures of the above applications are incorporated herein by reference.

GOVERNMENT CLAUSE

This invention was made with government support under 1403004 and 1404436 awarded by the National Science Foundation. The government has certain rights in the invention.

FIELD

The present disclosure relates to deriving central blood pressure via a standard automatic blood pressure monitor with cuff.

BACKGROUND

Tonometric devices for non-invasive monitoring of central blood pressure (BP) have been available for many years now. These devices either acquire a carotid artery tonometry waveform and calibrate it with brachial cuff BP levels for a "direct" measurement of central BP or obtain a similarly calibrated, but easier-to-measure, radial artery tonometry waveform and then apply a generalized transfer function (GTF) to the peripheral BP waveform for an indirect measurement of central BP. The devices have even been shown to provide added clinical value over traditional brachial cuff BP measurements in several research studies. Yet, because applanation tonometry of any artery is nontrivial, they have not reached patient care.

As a result, oscillometric devices for more convenient monitoring of central BP have recently been introduced. With reference to FIG. 1A, these devices employ a special automatic arm cuff to derive central BP generally in four steps. First, brachial BP levels are obtained in the standard way by slowly deflating (or inflating) the cuff and then estimating the values from the oscillogram (i.e., the variable cuff pressure oscillation amplitude versus cuff pressure function). Second, a fixed-amplitude cuff pressure oscillation or "pulse volume plethysmography (PVP)" waveform is measured by maintaining a constant cuff pressure around the diastolic level for up to 30 seconds or even above the systolic level by up to 35 mmHg. Third, a brachial BP-like waveform is derived by calibrating the PVP waveform with the brachial BP levels. Fourth and finally, central BP is computed from the peripheral waveform typically via a GTF. The error in the measured central BP can be substantial. Like the tonometric devices, the main error source is the error in the brachial BP levels used for calibration. This latter error can be large, because automatic arm cuffs employ population average methods to estimate the brachial BP levels. A secondary error source may be error arising from the use of a one-size-fits-all GTF.

Therefore, it is desirable to achieve accurate central BP monitoring via a standard automatic arm cuff. This section provides background information related to the present disclosure which is not necessarily prior art.

SUMMARY

This section provides a general summary of the disclosure, and is not a comprehensive disclosure of its full scope or all of its features.

The main idea is to compute central blood pressure (BP) from the cuff pressure waveform obtained with a standard automatic arm cuff rather than a special cuff, which performs additional cuff inflations/deflations.

In a general embodiment, a method is presented for determining central BP for a subject using an automatic cuff BP monitor. The method includes: measuring cuff pressure using an automatic cuff BP monitor during one of inflation or deflation of cuff and thereby yielding a cuff pressure waveform; extracting features of the measured waveform including the high pass filtered cuff pressure waveform ("variable-amplitude cuff pressure oscillation waveform"); and computing central BP values from the features. The computation may be defined by applying machine learning (e.g., deep learning) to a training dataset of cuff pressure waveforms and reference central BP measurements from a cohort of subjects. The computation may alternatively be based on physiologic modeling.

In a more specific embodiment, a method is presented for determining central BP for a subject using an automatic cuff BP monitor. The method includes: measuring cuff pressure using an automatic cuff BP monitor during one of inflation or deflation of cuff and thereby yielding a cuff pressure waveform; estimating magnitude of brachial BP for the subject from the measured cuff pressure waveform; extracting a pulse volume plethysmography (PVP) waveform (i.e., a fixed-amplitude cuff pressure oscillation waveform) from the measured cuff pressure waveform; scaling the PVP waveform to the estimated magnitude of the brachial BP; and determining a central BP waveform for the subject using the scaled PVP waveform.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1A:
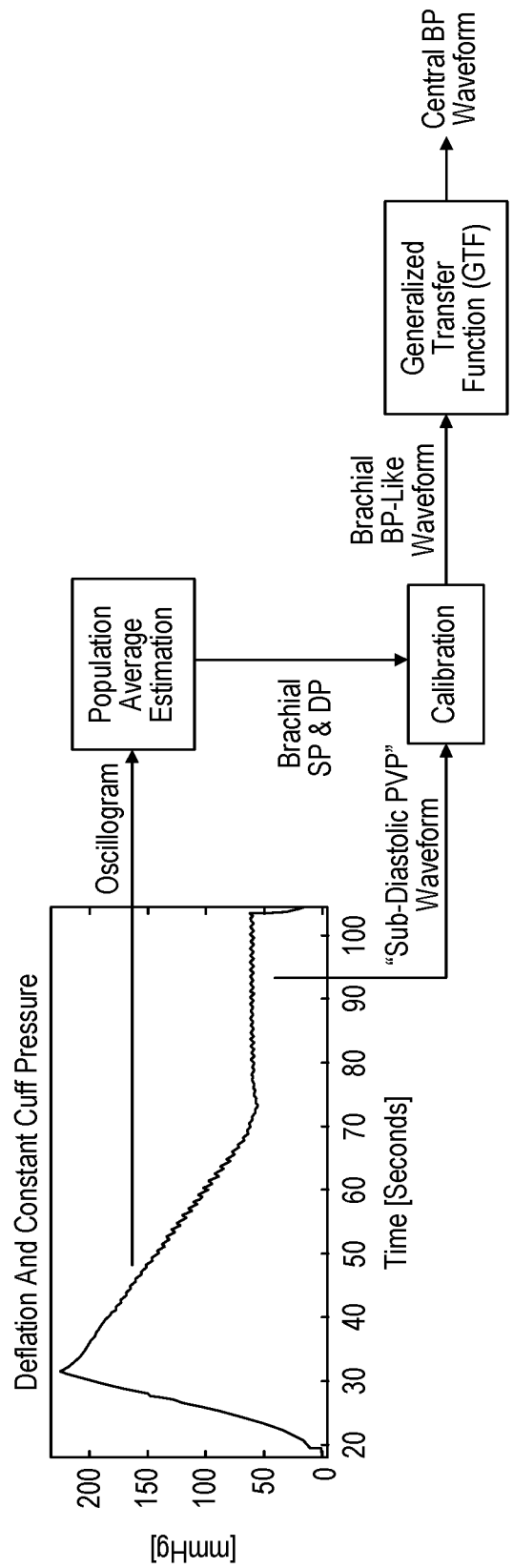
FIG. 1A is a diagram illustrating a conventional method for monitoring central blood pressure (BP) via a special automatic arm cuff device.
Figure 1B:
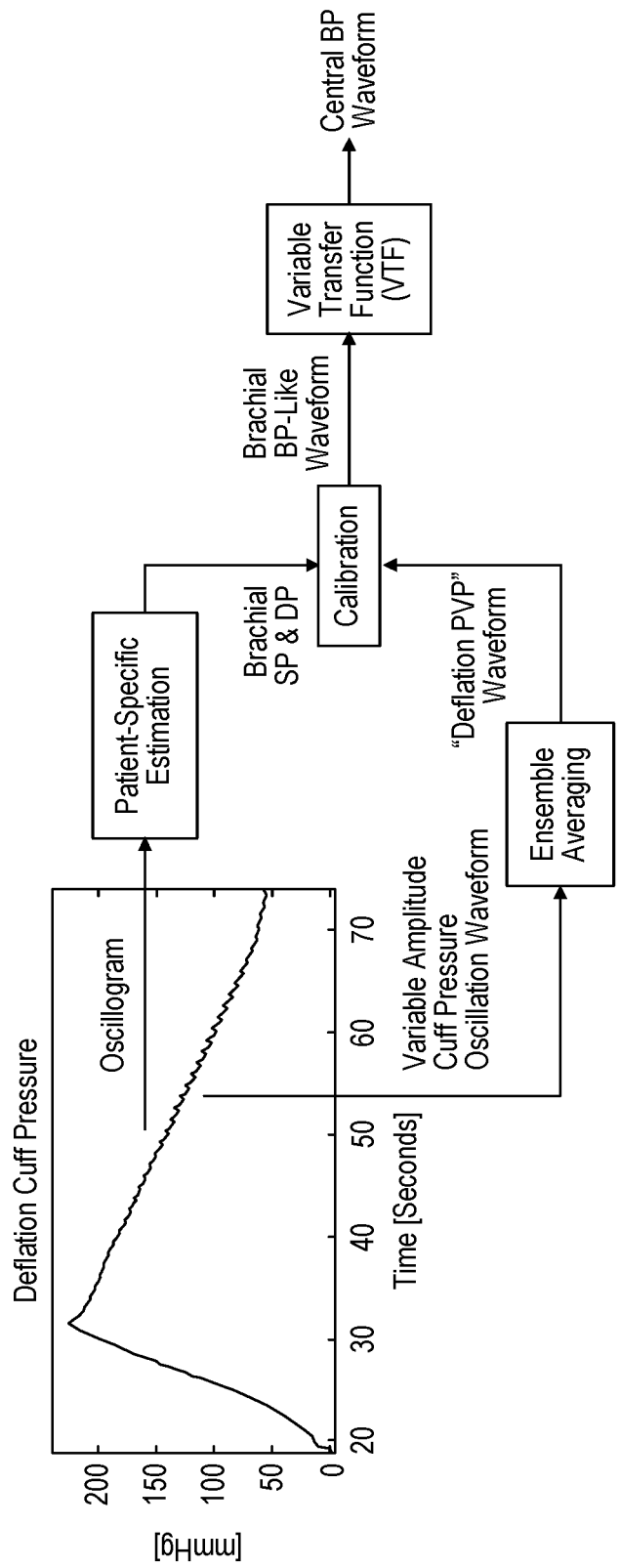
FIG. 1B is a diagram illustrating a new physiologic method for monitoring central BP via a standard automatic arm cuff device.

FIG. 1B illustrates a new method for monitoring central blood pressure (BP) of a subject using a standard automatic blood monitor device with an inflatable cuff (sometimes referred to as an automatic sphygmomanometer). During operation, the automatic blood monitor device measures cuff pressure during inflation and deflation of the cuff and generates a cuff pressure waveform 12. In an example embodiment, the cuff is inflated quickly and then deflated slowly.

The magnitude of the brachial BP for the subject is first estimated at 13 from the measured cuff pressure waveform. Specifically, the systolic and diastolic pressure are estimated. To do so, an oscillogram is derived from the cuff pressure waveform, where the oscillogram is the amplitude of oscillations in the measured cuff pressure as a function of the measured cuff pressure. The systolic pressure and the diastolic pressure are then estimated from the oscillogram. In one embodiment, the systolic pressure and the diastolic pressure are estimated using a population average estimation technique. In another embodiment, the systolic pressure and the diastolic pressure are estimated using a patient-specific estimation technique as further described below. Other techniques for estimating systolic pressure and diastolic pressure also fall within the broader aspects of this disclosure.

Additionally, a pulse volume plethysmography (PVP) waveform is extracted at 14 from the measured cuff pressure waveform using waveform scaling and ensemble averaging of multiple beats. Alternatively, a single representative beat may be selected from the measured cuff pressure waveform, such as the maximum oscillation beat, and used to construct the PVP waveform. Other types of extraction methods are also contemplated by this disclosure.

The PVP waveform is then scaled at 15 to the estimated magnitude of the brachial BP, thereby yielding a brachial BP-like waveform. For example, the PVP waveform is scaled so that its average maximum value is equal to brachial systolic pressure and its average minimum value is equal to brachial diastolic pressure. In some embodiments, the PVP waveform is preferably extracted from the measured variable-amplitude cuff pressure oscillation waveform during a low cuff pressure regime (e.g., <50 mmHg).

Lastly, the central BP waveform for the subject is determined at 16, for example using a transfer function, where the transfer function defines a relationship between the central BP waveform and the scaled PVP waveform. In one embodiment, a generalized transfer function (GTF) is used to compute central BP. In another embodiment, a variable transfer function (VTF) is used to compute central BP as further described below. Other techniques may also be applied to the scaled PVP waveform to convert it to a central BP waveform. For example, a regression equation involving features of the scaled PVP waveform (e.g., maximum value, area under curve) may be used to predict central BP.

Figure 2A:
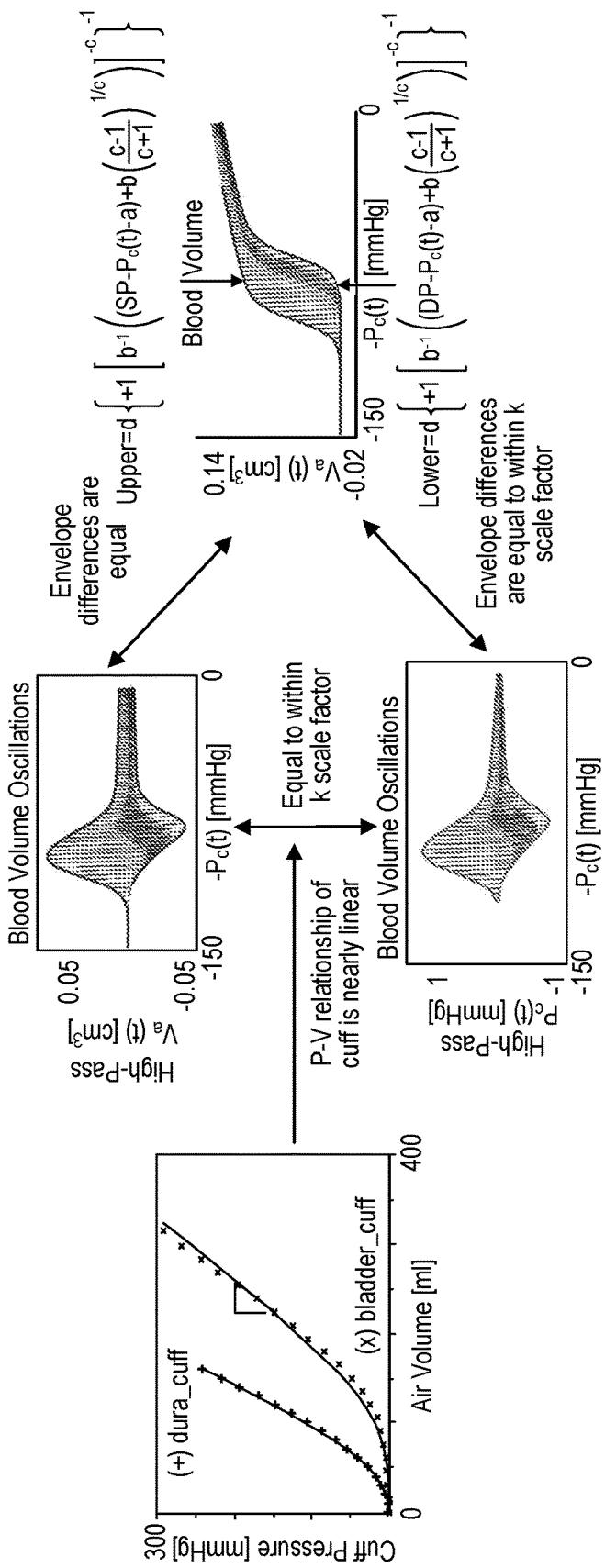
FIG. 2A is a diagram showing a patient-specific method for estimating brachial BP levels from a cuff pressure waveform obtained during conventional deflation by leveraging a physiologic model and parameter estimation.

With reference to FIG. 2A, the patient-specific method for estimating brachial systolic pressure (SP) and the diastolic pressure (DP) is described in more detail. The oscillogram (i.e., difference between the upper and lower envelopes in red) is represented with a physiologic model accounting for the nonlinear brachial artery blood volume-transmural pressure relationship as follows $$\underbrace{P_c^{pa}(t)}_{\text{Red Envelope Difference}} = \frac{e}{k \cdot d} \underbrace{\left\{ 1 + \left[ b^{-1}(SP - P_c(t) - a) + b\left(\frac{c-1}{c+1}\right)^{1/c} \right]^{-c} \right\}^{-1}}_{\text{Nonlinear relationship at systole}} -$$

$$e \underbrace{\left\{ 1 + \left[ b^{-1}(DP - P_c(t) - a) + b\left(\frac{c-1}{c+1}\right)^{1/c} \right]^{-c} \right\}^{-1}}_{\text{Nonlinear relationship at diastole}}$$

In particular, the nonlinear relationship is represented with a sigmoidal function as justified by experimental data, and the model of the oscillogram is then specified as the nonlinear relationship evaluated at brachial SP (see upper envelope in right plot of FIG. 2A) minus the nonlinear relationship evaluated at brachial DP (see lower envelope in same plot). This model arises from two observations. First, the difference in the upper and lower envelopes of the blood volume waveform as a function of negative cuff pressure plot is essentially equivalent to the difference in the upper and lower envelopes of the blood volume oscillations (i.e., the high pass filtered blood volume waveform) as a function of negative cuff pressure plot (compare right and upper plots in FIG. 2A). Second, the cuff pressure-air volume relationship of actual cuffs is nearly linear over a wide range (see left plot in FIG. 2A). Hence, the unmeasured blood volume oscillations may be proportional to the measured cuff pressure oscillations (compare upper and lower plots in FIG. 2A) with a proportionality constant equal to k, which indicates the reciprocal of the compliance of the cuff. The model parameters represent brachial SP and DP and brachial artery mechanics [a, b, c, e]. In terms of the brachial artery compliance curve (derivative of the nonlinear relationship with respect to transmural pressure), a denotes the transmural pressure at which the curve is maximal; b and c indicate the width of the curve and extent of asymmetry about its maximum; and e goes with the amplitude of the curve. The parameter e is also determined by the reciprocal of the cuff compliance [k], which is assumed to be constant in accordance with experimental data (see again left plot in FIG. 2A). As buttressed by directly measured compliance curves, a is fixed so that the curve peaks near zero transmural pressure, and b is constrained by the value of c such that the curve is right-skewed. The remaining four patient-specific parameters (i.e., brachial SP, brachial DP, c, e) are then estimated by least squares fitting of the model to the oscillogram as seen in the equation below.

$$\min_{\{1,b,c,e,SP,DP\}} \sum_{t \in \substack{Deflation \\ Period}} \left[ p_c^{oa}(t) - e\left\{ 1 + \left[ b^{-1}\left((SP - P_c(t) - a) + b\left(\frac{c-1}{c+1}\right)^{\frac{1}{c}}\right)\right]^{-c}\right\}^{-1} + e\left\{ 1 + \left[ b^{-1}\left((DP - P_c(t) - a + b\left(\frac{c-1}{c+1}\right)^{1/c}\right)\right]^{-c}\right\}^{-1}\right]^2$$

The user-selected variables (most notably, the a and b constraints) were established using a training dataset comprising cuff pressure waveforms for analysis and invasive reference brachial BP waveforms from cardiac catheterization patients. Further description for this patient specific method may be found in Liu, J. et al. Patient-specific oscillometric blood pressure measurement. *IEEE Trans. Biomed. Eng.* 63, 1220-1228 (2016) and Liu, J. et al. Patient-specific oscillometric blood pressure measurement: Validation for accuracy and repeatability. *IEEE J. Transl. Eng. Heal. Med.* 5, 1-10 (2017) which are incorporated in their entirety by reference.

The patient-specific method also outputs the entire brachial BP waveform via additional steps dictated by its underlying model. While this waveform is suitable for estimating mean BP (MP), it contains some artifact caused by inter-beat cuff pressure variations. Hence, another method is applied to extract a brachial BP-like waveform from the variable-amplitude cuff pressure oscillation waveform.

Figure 3A:
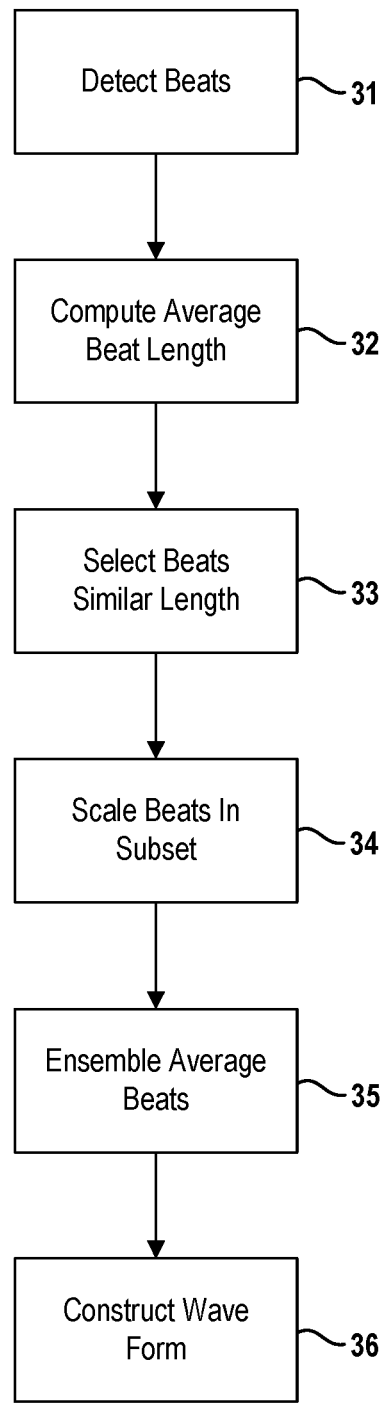
FIG. 3A is a flowchart depicting an example method for extracting a pulse volume plethysmography (PVP) waveform from the variable-amplitude cuff pressure oscillation waveform measured during slow cuff deflation ("deflation PVP" waveform) or inflation.

FIG. 3A illustrates an example method for extracting a pulse volume plethysmography (PVP) waveform from the cuff pressure waveform measured during slow cuff deflation (or slow cuff inflation). First, the beats are detected in the measured variable-amplitude cuff pressure oscillation waveform (i.e. the high pass filtered cuff pressure waveform) as indicated at 31. From the detected beats, an average beat length is computed at 32. A subset of the detected beats are then selected at 33, where beats in the subset have a beat length within a fixed variance of the average beat length. For example, beats within 20% of the average beat length are selected for inclusion in the subset. The beats in the subset are then equalized at 34 in amplitude and/or time via amplitude and time scaling. The scaled beats in the subset are ensemble averaged at 35. Finally, the ensemble averaged beat is used at 26 as the PVP waveform. It is to be understood that only the relevant steps of the methodology are discussed in relation to FIG. 3A, but that other steps may be needed to extract the PVP waveform.

Figure 3B:
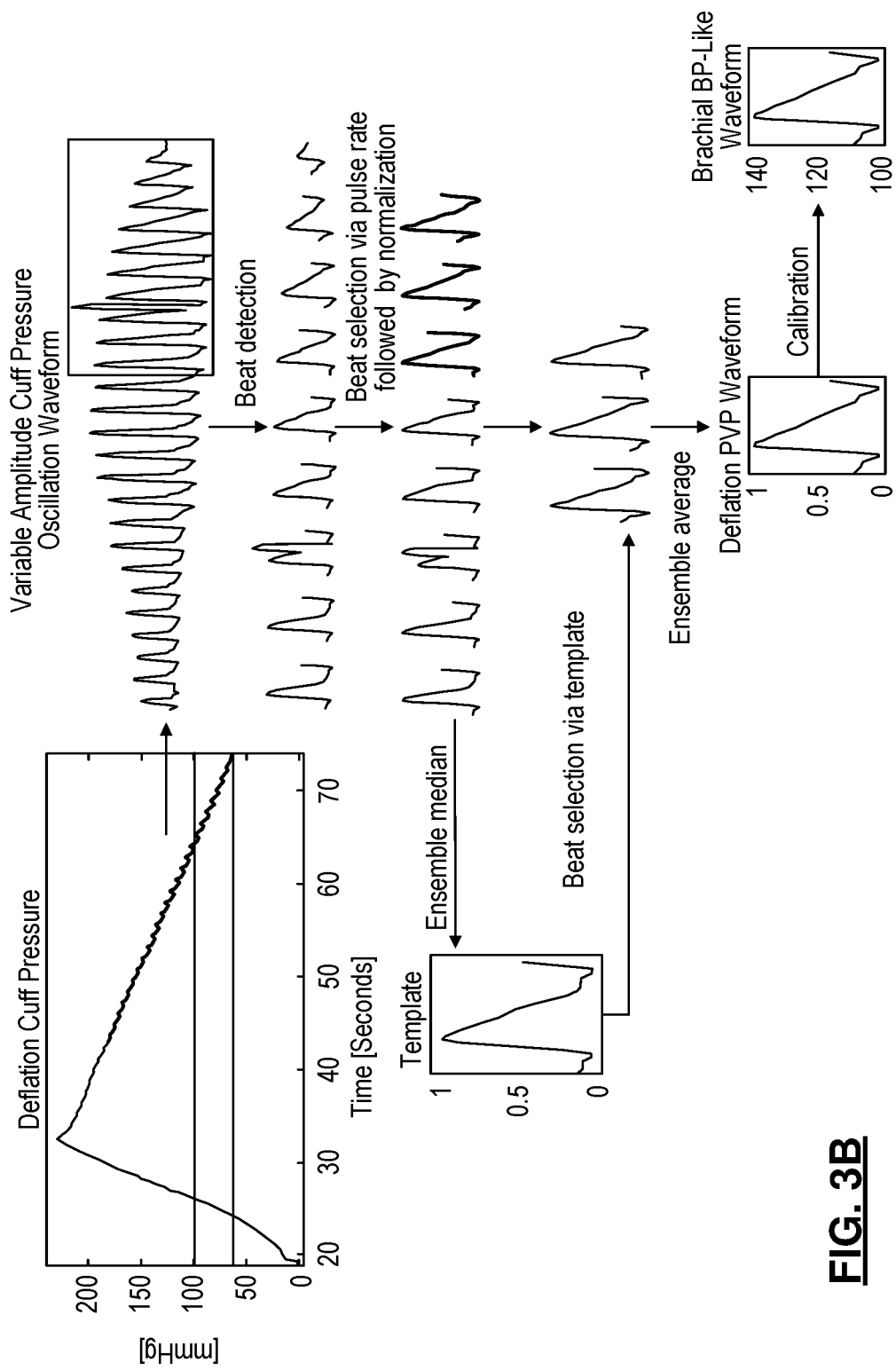
FIG. 3B is a diagram further illustrating an ensemble averaging/calibration method for extracting a brachial BP-like waveform from the variable-amplitude cuff pressure oscillation waveform obtained during conventional deflation.
Figure 4A:
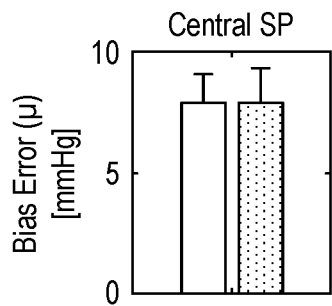
FIGS. 4A-4F shows central SP, pulse pressure (PP), and DP bias errors and precision errors of the patient specific method versus an office device (a population average method) in a testing dataset.
Figure 4B:
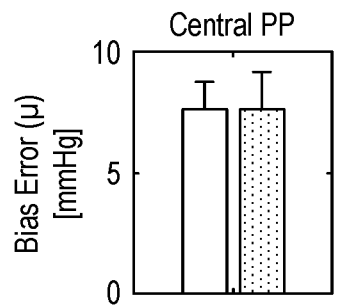
Figure 4C:
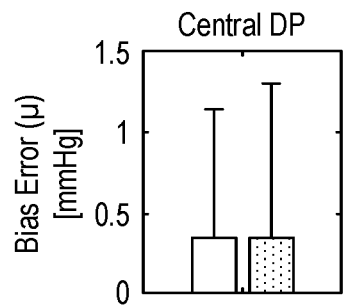
Figure 4D:
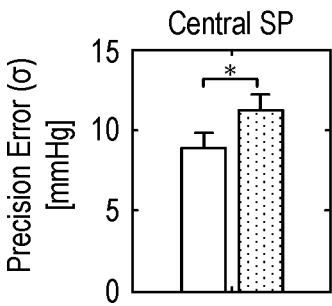
Figure 4E:
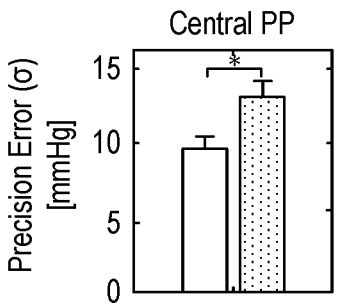
Figure 4F:
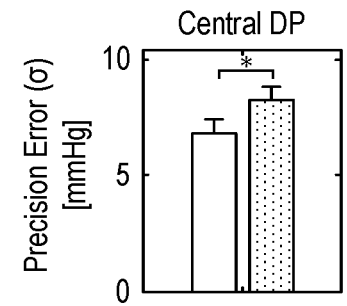
Figure 5A:
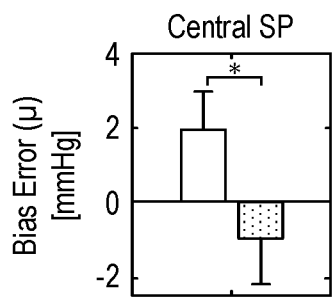
FIGS. 5A-5F shows central SP, pulse pressure (PP) and DP bias errors and precision errors of the physiologic method (which may use a standard automatic arm cuff) versus the conventional method (which used a special automatic arm cuff) in the testing dataset.
Figure 5B:
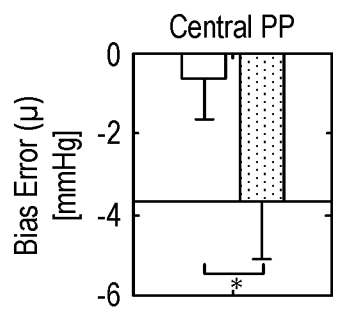
Figure 5C:
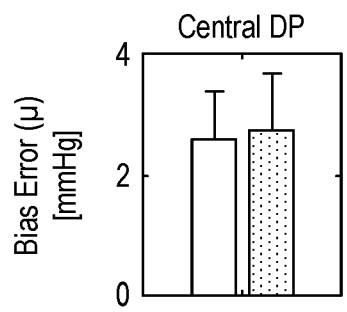
Figure 5D:
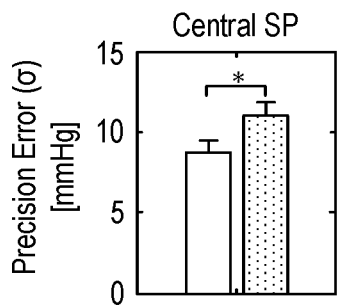
Figure 5E:
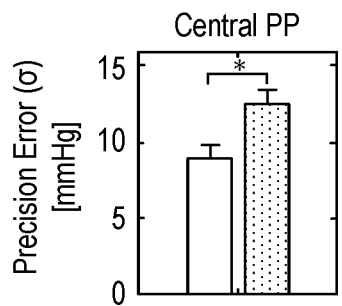
Figure 5F:
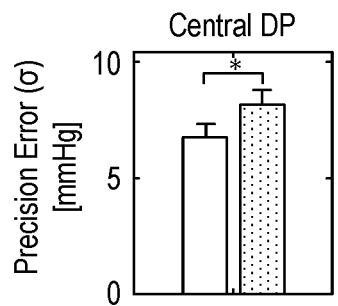
Figure 6A:
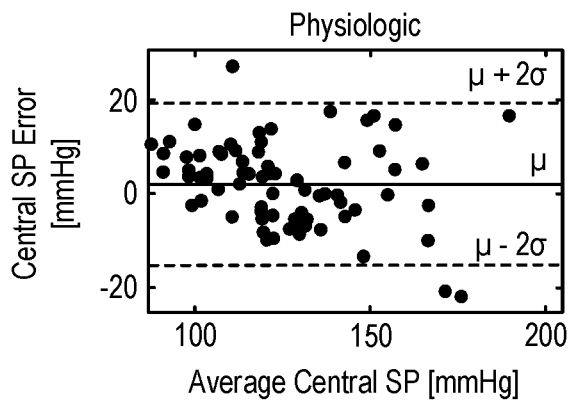
FIG. 6A-6F shows Bland-Altman plots of the central SP, PP, and DP errors of the physiologic method and conventional method in the testing dataset.
Figure 6B:
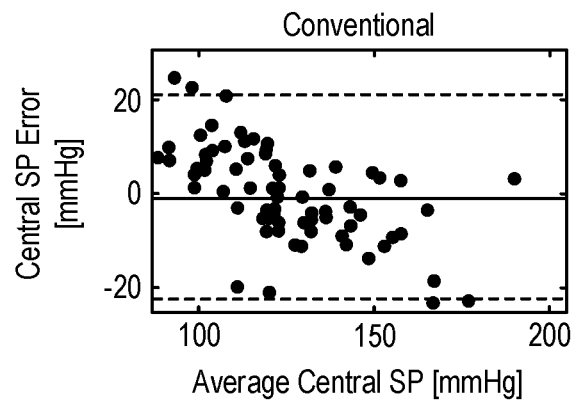
Figure 6C:
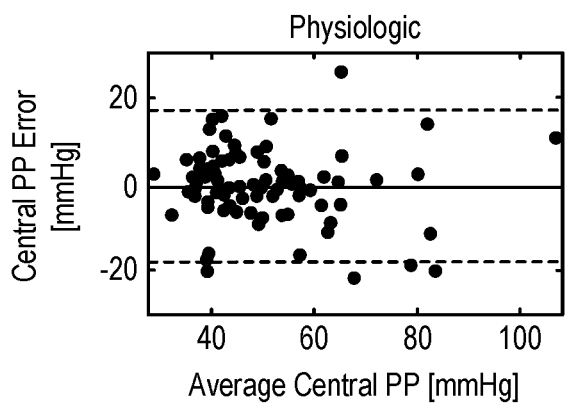
Figure 6D:
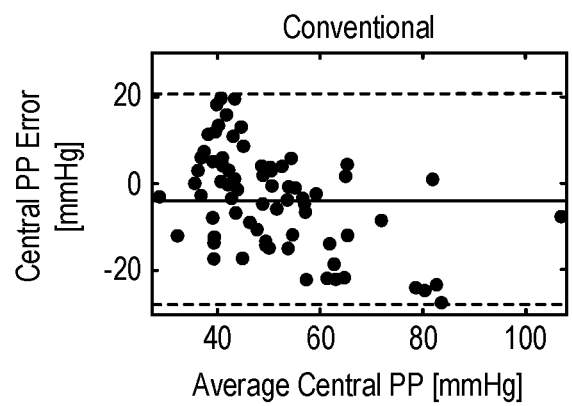
Figure 6E:
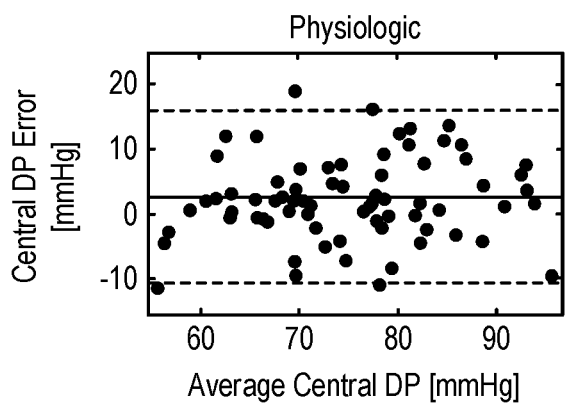
Figure 6F:
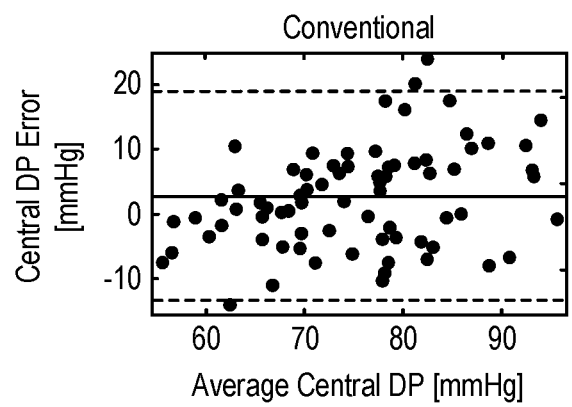
Figure 7A:
FIGS. 7A-7C show central SP, PP, and DP bias errors of the patient-specific method versus the physiologic method versus the physiologic method with VTF replaced by GTF for low PP amplification (ratio of reference brachial PP to central PP) subgroups in the testing dataset.
Figure 7A:
Figure 7A:
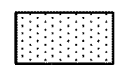
Figure 7A:
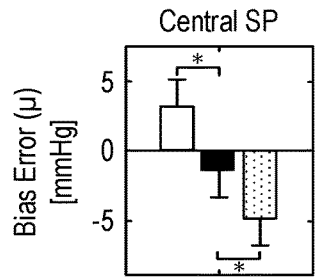
Figure 7B:
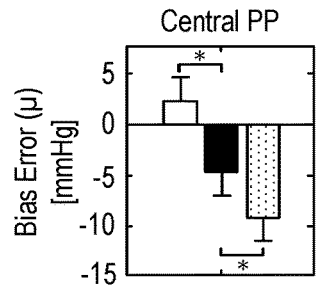
Figure 7C:
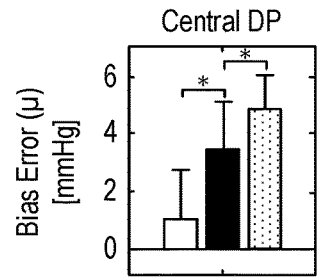
Figure 8A:
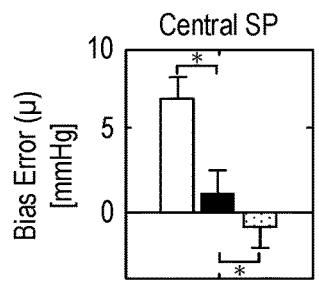
FIGS. 8A-8C show central SP, PP, and DP bias errors of the patient-specific method versus the physiologic method versus the physiologic method with VTF replaced by GTF for middle PP amplification (ratio of reference brachial PP to central PP) subgroups in the testing dataset.
Figure 8B:
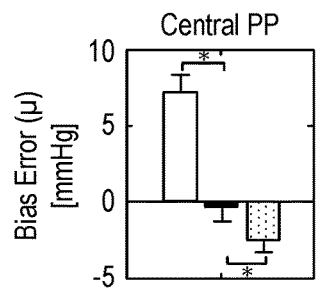
Figure 8C:
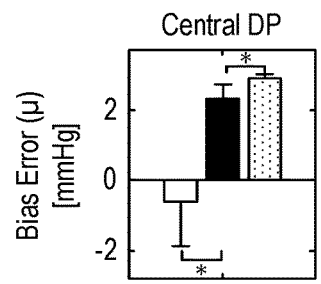
Figure 9A:
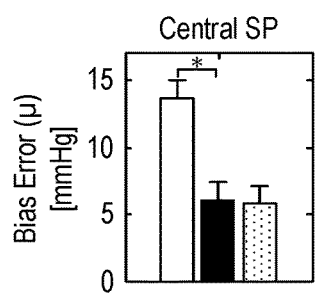
FIGS. 9A-9C show central SP, PP, and DP bias errors of the patient-specific method versus the physiologic method versus the physiologic method with VTF replaced by GTF for high PP amplification (ratio of reference brachial PP to central PP) subgroups in the testing dataset.
Figure 9B:
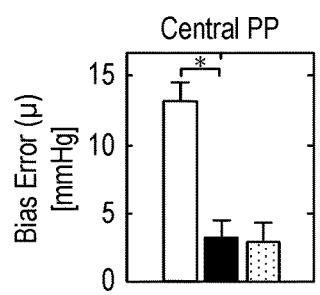
Figure 9C:
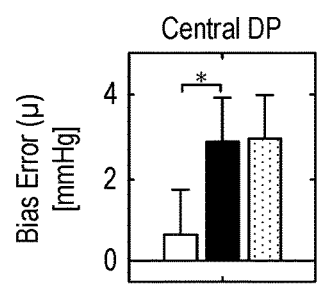

An example embodiment of an ensemble averaging/calibration method is further illustrated in FIG. 3B. The variable-amplitude cuff pressure oscillation waveform is analyzed over the cuff pressure range extending from (i) the minimum cuff pressure analyzed by the patient-specific method minus 40 mmHg to (ii) the minimum cuff pressure analyzed by the patient-specific method (shading). The waveform beats are detected. To eliminate anomalies, all waveform beats of lengths within 30% of the average beat length are selected in this embodiment. If fewer than three waveform beats meet this criterion, then the three waveform beats with lengths closest to the average beat length are selected. Each selected waveform beat, including 250 msec intervals before the first foot and after the last foot, is equalized by normalization to peak amplitude of one and feet amplitudes of zero. Time normalization could also be employed, if necessary, to further equalize the waveform beats. For example, each beat could be scaled in time so that the time interval from the first foot to peak is the same and the time interval from the peak to the second foot is the same. To further eliminate anomalies, a template waveform beat is constructed by computing the ensemble median of all selected waveform beats over the minimum beat length and then applying the same normalization. The three waveform beats with root-mean-squared-error (RMSE)<0.5 relative to the template waveform beat that are nearest to the minimum cuff pressure are selected (red traces). If less than three waveform beats meet this criterion, then the three waveform beats with the lowest RMSEs are selected. The ensemble average or median of the selected waveforms beats is computed over the minimum beat length and likewise normalized to yield the deflation PVP waveform. This waveform is then scaled to brachial SP and DP to yield a brachial BP-like waveform. All user-selected variables (e.g., 30% beat length and 0.5 RMSE thresholds) were defined with a training dataset but are not intended to be limiting.

This method for deriving the brachial BP waveform is simpler than the patient-specific method but still founded in physiology. In particular, each beat of the waveform not only varies in amplitude but also in shape. The shape variations are likewise due (in part) to the brachial artery compliance changes with transmural pressure. Since this compliance may be relatively constant over the higher transmural pressure range of oscillometry (e.g., 50 mmHg) wherein elastin fibers play a greater role in arterial wall mechanics, the shape of a beat of the waveform may better reflect that of the brachial BP waveform at lower cuff pressures (e.g., 50 mmHg). Hence, a deflation PVP waveform is preferably extracted from the variable-amplitude waveform over the lower cuff pressure range via robust ensemble averaging and calibrated to the brachial BP levels.

Figure 2B:
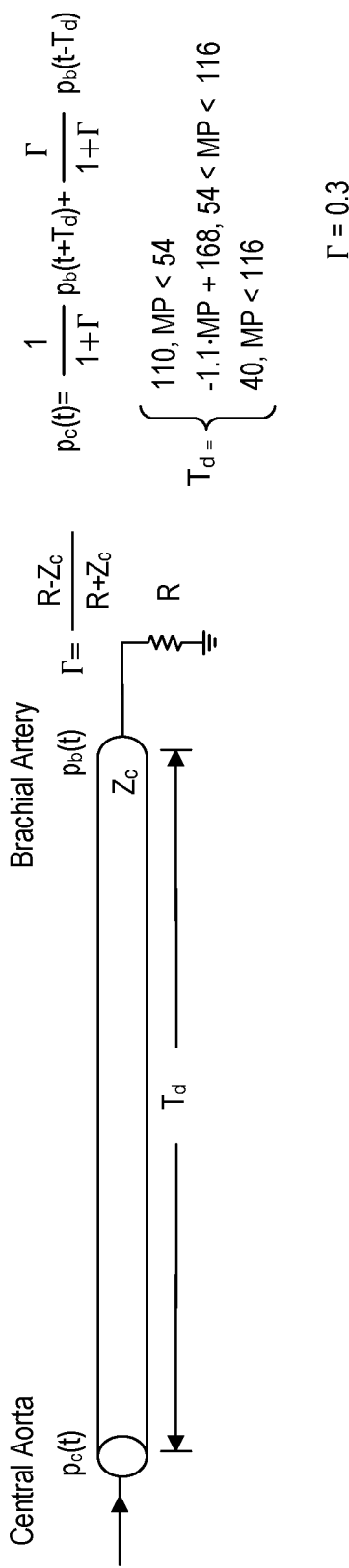
FIG. 2B is a diagram of a variable transfer function method for converting the brachial-like BP waveform to the central BP waveform.

In one embodiment, a VTF is used to convert the scaled PVP waveform to a central BP waveform as seen in FIG. 2B. The method is based on a physiologic model of arterial wave reflection, i.e., a tube-load model. Briefly, the tube accounts for the inertance [L] and compliance [C] of the large artery segment between the ascending aorta and brachial artery and thus offers constant characteristic impedance $[Z_c=\sqrt{(L/C)}]$ and permits waves to travel along it with constant pulse transit time $[T_d=\sqrt{(LC)}]$. The load accounts for the small artery resistance [R]. Waves traveling in the forward direction along the tube are reflected in the opposite direction at the terminal load with a constant reflection coefficient [Γ=

$(R-Z_c)/(R+Z_c)]$ so as to mimic the well-known amplification of brachial pulse pressure (PP) relative to central PP.

According to this VTF model, the transfer function relating the brachial BP waveform [$p_b(t)$] (i.e., BP at the tube end) to the central BP waveform [$p_c(t)$] (i.e., BP at the tube entrance) may be defined in terms of two parameters, $T_d$ and $\Gamma$ (see transfer function equation in the time-domain in FIG. 2B). This transfer function is often insensitive to $\Gamma$. Hence, this parameter could be fixed to a nominal value without significantly compromising accuracy. On the other hand, $T_d$ is a vital transfer function parameter. In particular, application of the transfer function predicts high PP amplification (ratio of brachial PP to central PP) when $T_d$ is large and low PP amplification when $T_d$ is small. It is well known that pulse transit time is strongly related to mean pressure (MP) and other variables. Hence, $T_d$ may be reasonably predicted from readily available measurements and thereby adapt to some extent to the inter-subject and temporal variations in PP amplification. The nominal value for $\Gamma$ and the prediction equation for $T_d$ in FIG. 2B were established using a training dataset. The $T_d$ prediction equation capitalizes on the inverse relationship between pulse transit time and MP, which is due to slack collagen fibers in the arterial wall and aging. Note that since this equation is fixed for all patients, the transfer function is not patient-specific. However, the equation allows for a transfer function that can vary (as opposed to the conventional GTF) and is simple enough that it may generally hold. So, first, MP, computed as the time average of the brachial BP-like waveform over its foot-to-foot interval, is used to predict $T_d$. Then, the fully defined VTF is applied in the time-domain to the entire brachial BP waveform to compute the central BP waveform.

To investigate the proposed method for measuring the central BP waveform, patients admitted for diagnostic cardiac catheterization at Taipei Veterans General Hospital (Taiwan) were studied. The study procedures were approved by the hospital's IRB and conformed to the principles of the Declaration of Helsinki. Written, informed consent was obtained from each patient.

Briefly, all patients had inter-arm cuff BP differences of no more than 3 mmHg. A high-fidelity catheter with one or two micro-manometers (SPC-320 or SSD-1059, Millar Instruments, USA) was positioned in the ascending aorta and brachial artery to sequentially or simultaneously measure gold standard reference central and brachial BP waveforms. An appropriately sized, inflatable cuff of a special office device (WatchBP Office, Microlife AG, Switzerland or VP-1000, Omron Colin, Japan) was placed properly over the other brachial artery to measure the cuff pressure waveform via conventional deflation, a PVP waveform via maintenance of the cuff pressure at 60 mmHg ("sub-diastolic PVP" waveform) for 30 sec, and the brachial BP levels estimated by the device. All of these cuff measurements were obtained during each sequential BP waveform measurement or the simultaneous BP waveform measurement under baseline and/or sublingual nitroglycerin conditions. Repeated cuff measurements were made per condition for the Microlife device.

All sets of cuff pressure and BP measurements were screened for possible exclusion from subsequent analysis. The exclusion criteria for a measurement set were: (a) substantial artifact due to motion or otherwise in at least one waveform as determined by visual inspection; (b) MP difference in brachial and central BP waveforms, which are sequentially (as opposed to simultaneously) measured, exceeding 5 mmHg; or (c) BP waveforms, which are sequentially measured, during the transient nitroglycerin condition. The latter two criteria ensured that the central and brachial BP waveforms were indicative of the same physiologic state. About 120 patients were included for study, and a total of 209 measurement sets from 87 patients remained for analysis. The measurement sets from 36 of the patients were previously used to develop the patient-specific method for estimating brachial BP levels, so these data constituted the training dataset. The measurement sets from the other 51 patients formed the testing dataset. Table 1 shows the measurement and patient characteristics for the datasets. Note that the testing dataset included Omron and Microlife cohorts.

TABLE 1

|  | Training | Testing Cohort1 | Cohort 2 |
|---|---|---|---|
| Measurements | Device | | |
| Device measurements | Microlife deflation cuff pressure waveform + office brachial BP levels + sub-diastolic PVP waveform | Omron | Microlife |
| Reference | Invasive brachial and central BP waveforms | | |
| # of subjects | 36 | 43 | 8 |
| # of baseline measurements | 36 | 38 | 8 |
| # of nitroglycerin measurements | 36 | 13 | 8 |
| # of repeated measurements | 70 | 0 | 10 |
| Total # of measurements | 142 | 51 | 26 |
| Patients | | | |
| Type | Cardiac catheterization | | |
| Age [years] | 64.9 ± 12.6 | 57.1 ± 13.9 | 71.2 ± 12.7 |
| Weight [kg] | 75.7 ± 13.1 | 69.7 ± 12.1 | 69.3 ± 14.9 |
| Height [cm] | 161.8 ± 8.2 | 163.5 ± 8.8 | 161.2 ± 10.5 |
| Waist circumference [cm] | 90.4 ± 12.5 | 92.6 ± 11.5 | 94.5 ± 11.0 |
| Men [%] | 75.7 | 75.0 | 75.0 |
| Smoking [%] | 18.9 | 20.5 | 25.0 |
| Hypertension [%] | 59.5 | 56.8 | 87.5 |
| Type 2 Diabetes mellitus [%] | 29.7 | 31.8 | 50.0 |
| Dyslipidemia [%] | 37.8 | 40.9 | 37.5 |
| Coronary artery disease [%] | 59.5 | 56.8 | 62.5 |
| Chronic renal failure [%] | 2.7 | 2.3 | 12.5 |
| α-Blockers [%] | 13.5 | 11.4 | 25.0 |
| β-Blockers [%] | 43.2 | 38.6 | 62.5 |
| Calcium channel blockers [%] | 48.6 | 40.9 | 25.0 |
| Diuretics [%] | 18.9 | 20.5 | 37.5 |
| Antiplatelet agents [%] | 86.5 | 70.5 | 87.5 |

The training dataset was analyzed to develop the sub-methods of the physiologic method. The patient-specific method was rigorously developed as described elsewhere; whereas simple, but sub-optimal, approaches were applied here to develop the ensemble averaging and VTF methods. For comparison, the training dataset was also used to build the conventional method of FIG. 1A.

To develop the ensemble averaging method, the variable-amplitude cuff pressure oscillation waveforms and sub-diastolic PVP waveforms were analyzed. In particular, the user-selected variables of the method were established so that the RMSE of the deflation PVP waveform extracted from the variable-amplitude waveform with respect to the corresponding sub-diastolic PVP waveform (formed by conventional ensemble averaging and amplitude normalization for the average waveform beat but not the individual waveform beats) was <0.1.

To develop the VTF method, the sub-diastolic PVP waveforms, simultaneously measured central BP waveforms, and invasive brachial BP waveforms were analyzed. The sub-diastolic PVP waveforms were first calibrated to invasive brachial DP and SP so as to avoid over-fitting the transfer function to random calibration error. For each pair of brachial BP-like and central BP waveforms, $\Gamma$ and $T_d$ were estimated by least squares fitting of the model predicted central BP waveform (see FIG. 2C) to the measured central BP waveform. The value of $\Gamma$ was then set to the average of the $\Gamma$ estimates. A $T_d$ prediction equation was created using the $T_d$ estimates as the dependent variable and various measurements as the independent variables. The investigated independent variables included the invasive brachial BP levels (to likewise prevent overfitting of the equation), the brachial artery compliance parameter estimates of the patient-specific method, pulse rate, and patient anthropomorphic data such as age, height, and arm circumference. Multivariate linear regression was employed, and the utility of the independent variables was assessed using a step-wise approach. MP was concluded to be the only independent variable in the final prediction equation (see FIG. 2C). The correlation coefficient between the predicted and measured $T_d$ was almost 0.6. PTT limits were thereafter added to the $T_d$ prediction equation to protect against gross MP estimation error (see FIG. 2B).

To develop the conventional method, various possible implementations were explored, and the best implementation was selected. In particular, the GTF was defined in terms of the tube-load model of FIG. 2B or an autoregressive exogenous input model. To set the model parameters of the GTF, the sub-diastolic PVP waveforms were calibrated to invasive brachial SP and DP, invasive brachial MP and DP, the brachial SP and DP obtained with the office device, or the brachial MP and DP obtained with this device. The selected GTF was based on the tube-load model with parameters set to the averages of the aforementioned $\Gamma$ and $T_d$ estimates. This parameter setting is justifiable, because the sub-diastolic (rather than deflation) PVP waveform was used and calibrated to invasive (instead of patient-specific) brachial SP and DP in the development of the VTF method. Note that this GTF must be evaluated as applied to the PVP waveform calibrated with the brachial SP and DP obtained with the office devices rather than an invasive catheter system. However, the office devices were likely developed based on reference auscultation BP measurements, which systematically underestimate invasive brachial SP and overestimate invasive brachial DP. Hence, prior to the PVP waveform calibration, the office brachial BP levels were corrected in terms of their bias error (see below). Such a bias correction allowed the GTF to serve its intended purpose of reducing PP amplification, significantly improved the central BP measurement accuracy of the conventional method, and could easily be implemented in practice. Finally and importantly, the other implementations of the conventional method did not improve the central BP waveform accuracy in the training or even testing datasets (results not shown).

The testing dataset was then analyzed to assess and compare the accuracy of the developed methods. The physiologic method as well as the physiologic method with the VTF replaced by the GTF were applied to the standard cuff pressure waveforms, whereas the conventional method was applied to the additional, sub-diastolic PVP waveforms calibrated to the brachial SP and DP estimated by the office device from the standard cuff pressure waveforms. For reasons mentioned above, prior to PVP waveform calibration, the office brachial BP levels were corrected so that their bias errors were the same as those of the patient-specific method for each of the two patient cohorts. The errors between the resulting brachial and central SP, MP, DP, and PP measurements and the gold standard reference BP levels were quantified via the conventional bias error (i.e., mean of the errors) [$\mu$] and precision error (i.e., standard deviation of the errors) [$\sigma$]. The bias and precision errors for the lower, middle, and upper tertile PP amplification subgroups were also computed to investigate the added value of the VTF method.

The bias and precision errors of two methods were compared via paired t-tests and Pitman-Morgan tests, respectively. To generously account for multiple comparisons, a $p \leq 0.01$ was considered significant.

The training dataset was needed to develop the methods for investigation. However, the results from this dataset carry little meaning and did not offer additional insight. Hence, only the testing dataset results are provided.

TABLE 2

|  | SP [mmHg] | MP [mmHg] | DP [mmHg] | PP [mmHg] | PP Amplification (unitless) |
|---|---|---|---|---|---|
| Brachial | 134 ± 21 (99-192) | 96 ± 13 (72-129) | 71 ± 11 (43-101) | 63 ± 19 (33-113) | 1.2 ± 0.15 (0.99-1.7) |
| Central | 125 ± 23 (85-190) | 95 ± 13 (69-128) | 73 ± 10 (47-101) | 53 ± 20 (26-108) |  |

Values are average ± SD (minimum – maximum), SP, MP, and DP are systolic, mean and diastolic BP, respectively; PP, pulse pressure; and PP amplification, ratio of brachial PP to central PP.

Table 2 above shows the average±SD and range of reference brachial and central SP, MP, DP, and PP as well as PP amplification (ratio of brachial PP to central PP). All of the BP parameters varied widely. Most notably, central SP and PP ranged over 105 and 82 mmHg, respectively.

TABLE 3

|  | Brachial SP [mm Hg] | | Brachial DP [mm Hg] | | Brachial PP [mm Hg] | |
|---|---|---|---|---|---|---|
| Method | $\mu$ | $\sigma$ | $\mu$ | $\sigma$ | $\mu$ | $\sigma$ |
| Omron | -5.7 ± 1.2 | 10.7 ± 0.9 | 2.7 ± 1.1 | 9.5 ± 0.8 | -8.4 ± 1.5 | 12.9 ± 1.1 |
| Patient-specific | 0.7* ± 1.0 | 8.8* ± 0.7 | 3.5 ± 0.8 | 7.3* ± 0.6 | -2.8* ± 1.1 | 9.4* ± 0.8 |
| Microlife | -4.5 ± 1.2 | 10.6 ± 0.9 | 4.4 ± 0.6 | 5.4 ± 0.4 | -8.9 ± 1.5 | 13.2 ± 1.1 |
| Patient-specific | -3.4 ± 0.9 | 7.5* ± 0.6 | -1.1* ± 0.7 | 5.8 ± 0.5 | -2.3* ± 1.1 | 10.0* ± 0.8 |

*$p \leq 0.01$ compared to corresponding office device via paired t-test for bias error ($\mu$) and Pitman-Morgan test for precision error ($\sigma$)

Table 3 above shows the brachial SP, DP, and PP bias and precision errors (average±SE) of the patient-specific method and the office devices. The patient-specific method yielded significantly lower precision errors than the office devices and thereby afforded superior calibration. As expected, the patient-specific method also produced significantly lower bias errors. However, the office device bias errors could be corrected in practice (by e.g., adding and subtracting constant values from brachial SP and DP). Hence, in this study, the BP levels of the office devices were adjusted to make their bias errors equal to those of the patient-specific method.

FIGS. 4A-4F and 5A-5F respectively show the central SP, PP, and DP bias and precision errors (average±SE) of the patient-specific method versus the office device and of the physiologic method versus the conventional method aggregated over both cohorts. The precision errors for each cohort were along the lines of Table 3. The central BP errors of the patient-specific method and office device (i.e., the errors between the brachial BP levels measured by these methods and the reference central BP levels) represent the "starting point" errors prior to applying the transfer function. As expected, the central SP and PP bias errors were large and positive. While the two methods yielded the same bias errors due to the bias correction, the patient-specific method produced significantly lower precision errors. Comparing the precision errors to those in Table 3, it can be inferred that the main source of these errors is the calibration error rather than PP amplification variability. Application of the transfer function reduced the central SP and PP bias errors greatly but not the corresponding precision errors (compare FIGS. 4A-4F to FIGS. 5A-5F). The physiologic method afforded central BP bias errors of −0.6 to 2.6 mmHg and precision errors of 6.8 to 9.0 mmHg. These errors were significantly lower than those of the conventional method by 22% in terms of average RMSE. This error reduction was mainly due to improved PVP waveform calibration. FIGS. 6A-6F show Bland-Altman plots of the errors of the two featured methods for comparison.

FIGS. 7A-7C and 8A-8C and 9A-9C show the central SP, PP, and DP bias errors (average±SE) of the patient-specific method versus the physiologic method versus the physiologic method with the VTF replaced by the GTF for the low, middle, and high PP amplification subgroups, respectively. The precision errors were similar amongst the methods. The purpose of this figure is to reveal the value of the VTF method. The patient-specific method (which again measures brachial rather than central BP levels) yielded central SP and PP bias errors that were large and positive when PP amplification was high and that decreased appreciably with PP amplification. The GTF significantly decreased the central SP and PP bias errors by mitigating the overestimation of these BP levels when PP amplification was higher but substantially increased the errors by underestimating central SP and PP when PP amplification was low. The VTF provided significantly lower central SP and PP bias errors over the whole PP amplification range by decreasing the pulse transit time parameter of the tube-bad model transfer function with increasing MP. However, it was not always superior. While the VTF reduced or maintained the central SP and PP bias errors of the GTF, its added value overall was not large due to the higher precision errors of both methods. On the other hand, the patient-specific method yielded significantly lower central DP bias errors. Hence, the patient-specific DP could instead be used to improve central DP accuracy to a mild extent.

The ensemble averaging method yielded a RMSE of the deflation PVP waveform with respect to the corresponding sub-diastolic PVP waveform of 0.07±0.03. The time average of the deflation PVP waveform calibrated with patient-specific brachial SP and DP yielded MP bias and precision errors of 4.3 and 7.8 mmHg. Finally, the $T_d$ prediction equation produced a correlation coefficient between predicted and measured $T_d$ of 0.5.

With reference to FIG. 1B, this disclosure presented a "physiologic method" to monitor the central BP waveform via a standard automatic arm cuff. The method applies three sub-methods in succession as follows. First, a patient-specific method that is introduced is employed to estimate brachial BP levels from a cuff pressure waveform obtained during conventional deflation by leveraging a physiologic model and optimization (see FIG. 2A). This method can yield more accurate brachial BP levels than current population average methods, as shown previously and herein (see Table 3), and may thus reduce the major calibration error of most current tonometric and oscillometric devices for non-invasive monitoring of central BP. Then, an ensemble averaging/calibration method is applied to the same cuff pressure waveform so as to extract a "deflation PVP" waveform and scale it to patient-specific brachial SP and DP (see FIG. 3B). This simple, yet physiology-based, method may eliminate the need for the additional step performed by all available oscillometric devices in which the cuff is maintained at a constant pressure to measure the PVP waveform, which is then calibrated to the population average brachial BP levels. Finally, a VTF method can be employed to convert the brachial BP-like waveform to the central BP waveform. The method defines the transfer function in terms of the pulse transit time ($T_d$) and wave reflection coefficient (Γ) parameters of a physiologic model (see FIG. 2B). The reflection coefficient is set to a nominal value, as the transfer function is often insensitive to this parameter, while the pulse transit time, which has significant impact on the extent to which the transfer function reduces PP amplification, is predicted based on its well-known inverse relationship with MP (see FIG. 2B). This simple, physiologic modeling method may thus adapt the transfer function to BP-induced changes in arterial stiffness unlike the GTF, which is utilized by most of the current tonometric and oscillometric devices. In this way, central BP could be measured—for the first time—both reliably and in the exact same way as traditional brachial cuff BP.

The physiologic method was developed and evaluated for measuring the central BP waveform using data from cardiac catheterization patients (see Table 1). These data included the cuff pressure waveform obtained during conventional deflation, the brachial BP levels estimated from this waveform by popular office devices, a "sub-diastolic PVP" waveform obtained during constant inflation at 60 mmHg, and gold standard invasive reference central and brachial BP waveforms. In the testing dataset, the reference BP parameters varied widely (e.g., central SP ranged from 85 to 190 mmHg) mainly due to differing degrees of patient arterial stiffness (see Table 2). The precision errors between the brachial SP and PP computed by the office device and reference central SP and PP were 11.3 and 13.2 mmHg, respectively. These high "starting point" errors together with the wide BP parameter range underscored the challenge presented by the testing dataset.

The physiologic method yielded central SP, DP, and PP bias errors within 2.6 mmHg in magnitude and precision errors within 9 mmHg. These errors nearly satisfied the AAMI limits of 5 and 8 mmHg, though an AAMI data collection protocol was not employed.

Additionally, the physiologic method was compared to the conventional oscillometric method in which a GTF is applied to a sub-diastolic PVP waveform calibrated with office brachial BP levels to derive the central BP waveform. Since the GTF was built using invasive brachial SP and DP, the office devices were likely built using auscultation rather than invasive BP as the reference, and there is systematic error between the two reference methods, the bias errors of the office brachial BP levels (see Table 3) were first corrected to be the same as the patient-specific method. A GTF defined by the tube-load model in FIG. 2B, but with average values for both parameters, was then applied. Note that the bias correction was necessary to improve the accuracy of the conventional method and could be performed in practice. Importantly, other possible implementations of the conventional method (i.e., different PVP calibration procedures with and without bias correction and different GTFs) did not measure central BP levels more accurately. Hence, the employed conventional method may represent the best possible implementation.

Compared to the conventional method, the physiologic method produced significantly lower central SP, DP, and PP errors. Overall, the physiologic method yielded a 22% error reduction. The improved calibration afforded by the patient-specific method for measuring brachial BP levels was the main contributor to the reduction (see Table 3). The transfer function adaptation to BP-induced arterial stiffness changes offered by the VTF method was a secondary contributor and was most helpful relative to the GTF method in patients with low PP amplification where it was able to reduce the average central BP RMSE by 10%. The VTF method did not reduce the error compared to the GTF method in patients with high PP amplification, as the Td prediction via MP actually underestimated Td on average. Hence, despite being imperfect, the simple VTF method was still good enough to yield an improvement in central BP measurement accuracy in patients not used in its development. Further, the deflation PVP waveforms produced by the ensemble averaging method were similar enough to the sub-diastolic PVP waveforms that they hardly impacted the central BP errors (results not shown).

Other methods for central BP monitoring via an automatic arm cuff are available that instead obtain a supra-systolic PVP waveform and/or compute central BP from a calibrated PVP waveform without using a GTF. One method applies a transfer function based on the tube-load model in FIG. 2B to a calibrated, supra-systolic PVP waveform to derive the central BP waveform. The interesting idea is that, when the brachial artery is occluded by the supra-systolic cuff inflation, the forward and backward waves will be equal in magnitude. In this way, $\Gamma$ is correctly determined as unity. However, the transfer function is often insensitive to $\Gamma$, as we have mentioned, and whether the more important $T_d$ can be well determined from the proposed time delay between systolic PVP peaks or not is less certain. Further, the main source of error is the calibration rather than the transfer function, and the supra-systolic PVP waveform is small and thus susceptible to noise. Another method applies a multiple regression equation to several features of a calibrated, sub-diastolic PVP waveform of about 30 sec in duration to predict central SP and PP. This equation can yield significantly smaller central PP errors than a GTF by effectively reducing the calibration error. The reported precision errors of the method are also lower than those herein for the physiologic method, but the patient data for evaluation were not the same. The error differences could also be explained by the fact that the central BP waveforms derived by the physiologic method were obtained from single cuff deflation measurements, whereas the central BP levels predicted by the regression method represented the average of two cuff deflation measurements. Such averaging can reduce the precision error by a factor of up to $1/\sqrt{2}$. In any case, future comparisons of the physiologic method with other methods should be performed using the same data and analyses to obtain a conclusive assessment of their relative accuracy.

Even if other methods prove more accurate than the physiologic method in head-to-head comparisons, the difference would presumably have to be large enough to justify their additional cuff inflation. Automatic arm cuffs are already cumbersome enough to use. Requiring a prolonged sub-diastolic PVP waveform measurement, which could approximately double the measurement time, or a supra-systolic PVP waveform measurement, which is uncomfortable to the subject, may reduce patient compliance for using the device. Conversely, a method for measuring central BP with an acceptable level of error, but without changing the traditional measurement procedure, could increase the adoption of central BP.

In conclusion, PP and SP are amplified in the brachial artery relative to the central aorta. So, it is central BP that truly affects cardiac performance. Moreover, central BP rather than brachial BP is a major determinant of the degenerative changes that occur in aging and hypertension. Hence, central BP could provide greater clinical value than brachial BP. While several studies have demonstrated the added value of central BP, the extent of the difference may be considered unsatisfying. One possible explanation is that non-invasive central BP measurements suffer from substantial error due to the error introduced by the calibration step, which can be similar in magnitude to the difference between central and brachial BP levels. Another explanation is that the tonometric devices that have long been available for non-invasive central BP monitoring are not convenient enough for central BP to be studied broadly. A physiologic method is introduced to both mitigate the calibration error and obtain central BP measurements in the exact same way as traditional automatic cuff BP measurements. It has been shown that this method can yield central BP measurements that agree with gold standard reference measurements to a significantly greater degree than some current non-invasive devices.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

Figure 10:
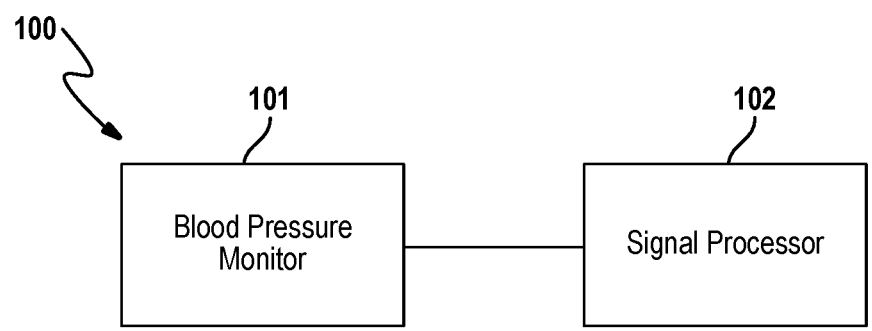
FIG. 10 is a block diagram of an apparatus for determining BP in accordance with the disclosed methods.

With reference to FIG. 10 the present disclosure also relates to an apparatus 100 for determining BP in accordance with the physiologic method set forth above. The apparatus 100 is comprised of a standard automatic arm cuff BP monitor 101 and a signal processor 102. During operation, the BP monitor 101 is configured to measure the cuff pressure waveform of the subject either during slow cuff inflation or deflation; whereas, the signal processor 102 implements the signal processing steps describe above which yield a central BP waveform. The mathematical model may be stored in a non-transitory computer memory associated with the signal processor 102.

In one embodiment, the BP monitor 101 is further defined as a sphygmomanometer or another automatic cuff device. The signal processor may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for determining central blood pressure for a subject using an automatic cuff blood pressure monitor, comprising:
   measuring, by the automatic cuff blood pressure monitor, cuff pressure of the automatic cuff blood pressure monitor during one of inflation or deflation of a cuff, thereby yielding a cuff pressure waveform;
   estimating magnitude of brachial blood pressure for the subject from the cuff pressure waveform;
   extracting a pulse volume plethysmography (PVP) waveform from the measured cuff pressure waveform, where the PVP waveform has a substantially fixed amplitude;
   scaling the PVP waveform to the estimated magnitude of the brachial blood pressure; and
   determining a central blood pressure waveform for the subject using the scaled PVP waveform.

2. The method of claim 1 wherein extracting the PVP waveform further comprises identifying a portion of the measured cuff pressure waveform having low cuff pressure and extracting the PVP waveform from the identified portion of the measured cuff pressure waveform.

3. The method of claim 1 wherein extracting the PVP waveform further comprises selecting representative beats of the measured cuff pressure waveform based on average beat length.

4. The method of claim 3 further comprises
   detecting beats in the measured cuff pressure oscillation waveform;
   computing an average beat length for the detected beats;
   selecting a subset of the detected beats, where beats in the subset have a beat length within a fixed variance of the average beat length; and
   ensemble averaging the beats in the subset.

5. The method of claim 4 further comprises scaling the beats in the subset so the beats are equal in at least one of amplitude or duration prior to the step of ensemble averaging.

6. The method of claim 1 further comprises extracting the PVP waveform by selecting a single representative beat from the measured cuff pressure oscillation waveform and constructing the PVP waveform using the single representative beat.

7. The method of claim 6 wherein the single representative beat has a maximum oscillation amongst beats in the measured cuff pressure oscillation waveform.

8. The method of claim 1 wherein the estimating magnitude of brachial blood pressure further comprises deriving an oscillogram from the cuff pressure oscillation waveform, and estimating systolic pressure and diastolic pressure for the subject from the oscillogram, where the oscillogram is an amplitude of oscillations in the measured cuff pressure as a function of the measured cuff pressure.

9. The method of claim 8 further comprises estimating magnitude of brachial blood pressure by representing the oscillogram with a mathematical model and estimating parameters of the mathematical model by fitting the mathematical model to the oscillogram, where the mathematical model is defined in terms of parameters with unknown values, parameters indicating systolic pressure and diastolic pressure and parameters that specify a nonlinear blood volume-transmural pressure relationship of the artery underneath the cuff of the automatic blood pressure monitor.

10. The method of claim 1 further comprises determining central blood pressure waveform using a transfer function, where the transfer function defines a relationship between the central blood pressure and the PVP waveform.

11. The method of claim 10 wherein the transfer function is defined by a tube-load model and parameters of the tube-load model include a pulse transit time and a wave reflection coefficient.

12. The method of claim 11 where pulse transit time is determined based on mean blood pressure and wave reflection coefficient is set to a nominal value.

13. The method of claim 1 further comprises determining central blood pressure waveform using a generalized transfer function.

14. The method of claim 1 further comprises determining central blood pressure waveform using a regression equation to predict central blood pressure from the scaled PVP waveform.

15. A method for determining central blood pressure for a subject using an automatic sphygmomanometer, comprising:
measuring cuff pressure using the automatic sphygmomanometer during deflation or inflation of a cuff of the automatic sphygmomanometer, thereby yielding a cuff pressure waveform;
deriving an oscillogram from the cuff pressure waveform, where the oscillogram is an amplitude of oscillations in the measured cuff pressure as a function of the measured cuff pressure;
estimating systolic pressure and diastolic pressure for the subject from the oscillogram;
extracting a pulse volume plethysmography (PVP) waveform from the cuff pressure waveform by one of amplitude or time scaling beats of the cuff pressure waveform and ensemble averaging the one of amplitude or time scaling beats of the cuff pressure waveform;
scaling the PVP waveform to the estimated systolic pressure and diastolic pressure; and
determining a central blood pressure waveform for the subject from the scaled PVP waveform using a transfer function, where the transfer function defines a relationship between the central blood pressure and the PVP waveform.

16. The method of claim 15 further comprises estimating systolic pressure and diastolic pressure by representing the oscillogram with a mathematical model and estimating parameters of the mathematical model by fitting the mathematical model to the oscillogram, where the mathematical model is defined in terms of parameters with unknown values, parameters indicating systolic pressure and diastolic pressure and parameters that specify a nonlinear blood volume-transmural pressure relationship of the artery underneath the cuff of the automatic sphygmomanometer.

17. The method of claim 15 further comprises extracting a pulse volume plethysmography (PVP) waveform from the measured cuff pressure waveform by detecting beats in the measured cuff pressure oscillation waveform;
computing an average beat length for the detected beats;
selecting a subset of the detected beats, where beats in the subset have a beat length within a fixed variance of the average beat length; and
ensemble averaging the beats in the subset.

18. The method of claim 16 wherein the transfer function is defined by a tube-load model and parameters of the tube-load model include pulse transit time and a wave reflection coefficient.

19. The method of claim 18 further comprises determining pulse transit time as a function of mean blood pressure.

20. A system for determining central blood pressure for a subject, comprising:
an automatic blood pressure monitor with an inflatable cuff, the automatic blood pressure monitor operates to measure cuff pressure during one of inflation or and deflation of the cuff and generates a cuff pressure waveform;
a brachial blood pressure estimator configured to receive the cuff pressure waveform and estimate systolic pressure and diastolic pressure for the subject from the cuff pressure waveform;
a PVP extractor configured to receive the cuff pressure waveform and extract a pulse volume plethysmography (PVP) waveform from the variable-amplitude cuff pressure oscillation waveform obtained by high pass filtering the measured cuff pressure waveform; and
a central transformer configured to receive the estimated systolic pressure and diastolic pressure and the extracted PVP waveform, the central transformer scales the PVP waveform to the estimated systolic pressure and diastolic pressure and determines a central blood pressure waveform for the subject using the scaled PVP waveform, wherein the brachial blood pressure estimator, the PVP extractor and the central transformer are implemented by a non-transitory computer readable medium comprising computer readable instructions executed by a computer processor.

* * * * *